(12) United States Patent
Guidot et al.

(10) Patent No.: US 6,552,228 B1
(45) Date of Patent: Apr. 22, 2003

(54) EXCHANGE AND TO THE RELEASE OF AN AMINE FROM ITS CARBAMOYL FLUORIDE

(75) Inventors: Gilbert Guidot, Massanes (FR); Christophe Rochin, Princeton, NJ (US); Laurent Saint-Jalmes, Meyzieu (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/609,216

(22) Filed: Jul. 5, 2000

(51) Int. Cl.$^7$ .................. C07C 209/00; C07C 19/08
(52) U.S. Cl. ..................................... 564/394; 570/128
(58) Field of Search .................. 564/394; 570/128

(56) References Cited

U.S. PATENT DOCUMENTS 4,481,370 A * 11/1984 Lin et al.

* cited by examiner

*Primary Examiner*—Alan L. Rotman
*Assistant Examiner*—Hector M Reys

(57) ABSTRACT

The present invention relates to a process for the treatment of an aryl carbamoyl fluoride comprising in its molecule at least one perhalogenated aliphatic carbon, which carbon carries at least one halogen atom to be exchanged with fluorine. This process comprises the stage of bringing the said carbamoyl fluoride into contact with hydrofluoric acid, the ratio of hydrofluoric [lacuna] to carbamoyl fluoride being maintained during the reaction at a value at least equal to 4, preferably to 5, and characterized in that the said ratio is at most equal to 11. Application to organic synthesis.

5 Claims, No Drawings

EXCHANGE AND TO THE RELEASE OF AN AMINE FROM ITS CARBAMOYL FLUORIDE

A subject-matter of the present invention is a process for the synthesis of compounds comprising both a perfluorinated carbon and an aniline functional group from its carbamoyl fluoride or from the corresponding isocyanate comprising chlorine atoms in place of fluorine atoms on the perfluorinated carbon.

The perfluorinated carbon is, in this case, a carbon of aliphatic nature, that is to say that it has $sp^3$ hybridization.

The present invention is more particularly targeted at a process for exchange and hydrolysis in the same reaction medium (that is to say without intermediate isolation), in particular based on hydrofluoric acid, and often in the same reactor.

In recent times and more specifically in the last decade, compounds comprising a perfluorinated aliphatic atom have become increasingly important in the field of agrochemistry and pharmaceuticals. This is because these perfluorinated products, generally comprising a perfluoromethyl or perfluoroethyl radical, have physiological properties which render the molecules which comprise them particularly active.

Numerous proposals have consequently been put forward for a process resulting in such products. Generally, the fluorinating agent is liquid hydrofluoric acid and the starting substrate is an isocyanate.

Mention may thus be made of the Occidental Chemical Corporation Patents No. EP-A-129 214 and the patent of the legal predecessor of the Applicant Company, namely the European patent filed on behalf of Rhône-Poulenc Spécialités Chimiques under No. 152 310. More recently, a European patent on behalf of Hoechst AG has been published under No. 639 556.

These documents makes known various alternative treatment forms in the hydrofluoric acid route.

According to this technique, the starting point is the protection of the amine functional group with an isocyanate functional group, for example by phosgenation. The carbon which in the final stage must be in a perfluorinated form is then chlorinated, generally in the radical fashion. Finally, the chlorinated compound thus obtained is subjected to a stage of chlorine/fluorine exchange in an anhydrous liquid hydrofluoric acid medium.

Two alternative forms have been explored to date: the release of the amine by means of heating in the presence of a large excess of hydrofluoric acid (anhydrous, of course) to give fluorophosgene or alternatively hydrolysis in a hydrofluoric acid medium with a relatively small amount of water.

The technique using the decomposition of carbamoyl fluorides to fluorophosgene exhibits the undoubted disadvantage of being accompanied by the evolution of fluorophosgene, the toxicity of which is supposed to be much greater than that of phosgene proper, which was used as a poison gas during the First World War.

Another disadvantage of this technique is the increased consumption of hydrofluoric acid, which is a relatively expensive reagent since it has to be used in a large excess.

The other techniques, namely techniques using in situ hydrolysis of the carbamoyl fluoride, give yields which are far from being excellent.

These low yields put a serious strain on the cost price of the final product and thus on the profitability of the complete operation.

Furthermore, the use of very large excesses of hydrofluoric acid, which involves a, to say the least, expensive recycling and inventory, as well as a subsequent dehydration, is also extremely penalizing as regards the cost price of the operation.

Finally, during the study which has led to the present invention, it was shown that even when the aromatic nucleus of the molecule was depleted in electrons, the reactivity of the carbamoyl fluorides was very high and resulted in many by-products which were harmful to the conversion yield, that is to say to the selectivity of the conversion.

It is for this reason that one of the aims of the present invention is to provide a process for obtaining aniline, additionally comprising a perfluorinated carbon atom, from the corresponding isocyanate or carbamoyl fluoride, which makes it possible to obtain high yields, that is to say exhibiting a conversion yield (CY) at least equal to 75%, preferably to 80%, more preferably to 90%.

Another aim of the present invention is to provide a process of the above type which makes it possible to have a degree of conversion (DC) at least equal to 80%, preferably at least equal to 90%.

Another aim of the present invention is to provide a process of the above type which makes it possible to have a reaction yield (RY=DC×CY) at least equal to 80%, preferably at least equal to 90%.

Another aim of the present invention is to provide a process of the above type which makes it possible to obtain a good yield with a minimum amount of hydrofluoric acid.

Another aim of the present invention is to provide a process of the above type which makes it possible to avoid the evolution, or at least to limit the evolution, of fluorophosgene.

These aims and others which will become apparent subsequently are achieved by means of a process for bringing a carbamoyl fluoride or an isocyanate into contact with hydrofluoric acid in the liquid phase and with water, characterized in that the ratio of the carbamoyl fluoride to the hydrofluoric acid (HF/substrate) is maintained for the duration of the reaction at a value at least equal to approximately 4, advantageously to 4.0, preferably to 5, more preferably to 6, and in that this ratio is advantageously at most equal to approximately 11, preferably to 10, more preferably to 8.

In the present description, the term "approximately" is employed to emphasize the fact that the values which follow it correspond to values which have been rounded off mathematically and in particular that, in the absence of a decimal point, when the figure or figures furthest to the right of a number are zeros, these zeros are positional zeros and not significant figures, unless, of course, it is otherwise specified.

As regards the exchange, the upper limit value has only economical importance. However, this low value of the upper limit has an effect on the addition of the water, as will be made known later.

This is because the studies which have led to the present invention have shown that, starting from the ratio of 4, the hydrofluoric acid plays a protective role with respect to side reactions involving the carbamoyl fluoride. Below these values, a large amount of side reactions, in particular formation of biuret, reaction in which heavy products are formed by condensation of the acyl halide with the aromatic nucleus, and the like, is observed.

It should be pointed out that the constraint relating to the ratio of 4 is strict and that, if the ratio is below this value or if the ratio falls below this value during the reaction, it is advisable to add hydrofluoric acid again in order to maintain this ratio above 4 during the reaction.

Thus, for example, if carbamoyl fluoride is introduced into the hydrofluoric acid in the form of an isocyanate and there are 3 chlorine atoms to exchange with fluorine, it will be necessary to add sufficient liquid hydrofluoric acid for this value to be observed throughout the reaction. This addition may just as easily be carried out at the beginning of as during the exchange. The first option is the simpler.

The simpler, in the preceding case, is to observe an overall ratio of the order of 8, namely 4, in order to provide for the reactions for exchange and for addition to the isocyanate functional group of the substrate, and 4, in order to provide for a good ratio of carbamoyl fluoride to hydrofluoric acid.

According to the present invention and in view of the constraints occasioned by a value of less than or equal to approximately 20 for the ratio of the carbamoyl fluoride to the hydrofluoric acid (HF/substrate), it has been shown that it is preferable for the addition of water to take place only at specific phases of the process.

If it is desired to control the amount of water in the medium, the hydrofluoric acid used is, of course, essentially anhydrous. However, it is possible to envisage the addition of water in the form of slightly hydrated hydrofluoric acid. The amounts of water targeted in the remainder of the description for the purpose of the hydrolysis comprise the possible amounts of water present as an impurity in the hydrofluoric acid. Generally, initially before the hydrolysis stage, use is made of hydrofluoric acids which comprise a total of at most 0.1 SA (with respect to the hydrolysis of the isocyanate or carbamoyl fluoride functional group), advantageously of at most 0.05, preferably of at most 0.02 SA, of water.

Thus, it is preferable to wait until there is at most one chlorine atom to be exchanged with the fluorine atom, to introduce the water. The time of the beginning of introduction of the water plays a not insignificant role with respect to the final yield (see Examples 3 and 4, where a difference of approximately 20 points in yield is observed).

In fact, it is possible to monitor the reaction with respect to the hydrochloric acid which is given off from the medium, in particular when pure liquid hydrofluoric acid is used, and, when there is only at most a single chlorine remaining to be exchanged with fluorine, it is possible to begin to envisage the addition of the water which will be used to hydrolyse the carbamoyl fluoride and to prevent the evolution of fluorophosgene. In fact, in the absence of water, evolution of fluorophosgene increases in proportion as the reaction mixture is exposed for a long time to temperatures of greater than 300° C., in particular of greater than 50° C. It should be remembered that fluorophosgene is a highly aggressive gas and a very troublesome impurity in gaseous acids and in particular hydrochloric acid.

Thus, the introduction of the water has a twofold effect:
with regard to the progress of the reaction, it is advisable to wait until the exchange is as complete as possible in order to maximize the yield,
with regard to the temperature, it is preferable for the introduction of the water to take place so as to minimize the time spent in the absence of water by the reaction mixture at temperatures of greater than 50° C.

It is even preferable, before carrying out the addition of water, to wait until only 0.5 and even 0.2 chlorine atom remains to be exchanged per molecule.

The ideal is even to wait until the exchange reaction is complete or virtually complete. The expression "complete or virtually complete" is understood to mean that there is, as residual halogen to be exchanged, only at most 0.02 chlorine per molecule of substrate; this corresponds to the fact that, in the medium or in the headspace of the reactor and during the subsequent quarter of an hour, the release of hydrohalic acid by exchange with fluorine is no longer detectable by conventional measuring means. Mention may be made, as an example of conventional measuring means, of the variation in pressure (for example: in the case of autogenous pressure) or in volume (for example: in the case of constant pressure), or more generally variation in the product PV, or alternatively, finally, quantitative determination of the residual substrates which have not completely exchanged, for example by GC (gas chromatography).

Thus, in the exchange phase, according to a preferred embodiment of the present invention, the substrate, halogenated by heavier than fluorine, generally chlorinated, is subjected to an exchange at a temperature at most equal to 50° C., advantageously at most equal to 40° C., preferably at a temperature at most equal to 20° C., more preferably at a temperature of less than the boiling point of liquid hydrofluoric acid, for a period of time sufficient to obtain an exchange which only leaves at most one chlorine atom to be exchanged per molecule.

It is desirable for this first phase to be carried out at a temperature at least equal to −20° C., advantageously to −10° C., preferably to −5° C.

Thus, this first phase is advantageously carried out at a temperature within the closed range [−10° C., 40° C.], advantageously within the closed temperature range (that is to say comprising the limits) between 0 and 40° C. ([0, 40]), the reaction is preferably completed at a temperature chosen from 20° C. to 40° C.

Once the partial exchange, which only leaves at most one chlorine atom to be exchanged (but it is desirable for only at most 0.2, advantageously at most 0.1, preferably at most 0.02, thereof to remain), has been achieved, after having optionally brought the reaction mixture to a temperature of between 30° C. and 50° C., the addition of the water is begun, advantageously gradually, the heat given off by the hydrolysis, optionally with addition of external heating, makes it possible at this point to increase the temperature and a temperature of between approximately 70 and approximately 100° C., generally between 80 and 90° C., is achieved.

If it is desired to avoid as far as possible the emission of fluorophosgene, it is recommended to add the water at low temperature. Thus, the addition of the water begins at a temperature at most equal to 50° C., advantageously at most equal to 30° C., preferably 25° C.

On completion of the addition of water, the reaction mixture can be maintained in this latter temperature range until the evolution of carbon dioxide gas has ceased but it is recommended to have a temperature at least equal to 70, advantageously to 80, preferably to 90° C., and at most equal to approximately 150° C., advantageously to 130° C., preferably to 120° C. The duration of this finishing phase depends on the temperature at this phase. As usual, the higher the temperature, the shorter the duration which makes it possible to bring the production of the product to completion. By way of indication, at 100° C., a duration of 5 to 8 hours makes it possible to obtain an excellent yield.

According to the present invention, in a batchwise implementation, it is considered that the evolution of carbon dioxide gas has ceased when, in the composition of the gases in the reactor headspace, the proportion of carbon dioxide gas does not rise by more than 1% (in absolute terms) over ¼ of an hour; if the operation is carried out at 70° C., it is advisable to multiply the period of time by two.

Although it is possible to use larger amounts of water (up to 3, indeed even 5, equivalents or SA), generally at most approximately 2 equivalents are used. In view of the fact that the presence of water can interfere with operations in which the hydrofluoric acid is possibly reprocessed and/or recycled in order to obtain it anhydrous, the amount of water used is limited and advantageously between 1 and 1.5 times the stoichiometric amount, preferably between 1.05 and 1.4 times the stoichiometric amount, the optimal value lies between 1.1 and 1.2.

When the isocyanate is used as starting material, which is most frequently the case, it is advisable to add it to the hydrofluoric acid; this makes it possible to better observe the low limit of the HF/substrate ratio.

In order to avoid any side reaction, it is very important for the reaction for the formation of the carbamoyl fluoride by reaction of the hydrofluoric acid with the isocyanate to take place by addition of the isocyanate to the hydrofluoric acid.

This addition is advantageously carried out at a temperature of less than 10° C.

A person skilled in the art will notice that this operation for the addition of isocyanate to hydrofluoric acid is entirely consistent with the restriction of maintaining a high ratio of the hydrofluoric acid to the isocyanate. This is because, if the mixing is carried out in the opposite sense, intermediate concentrations are involved which do not observe this restriction.

The reaction can be carried out under pressure and in particular under that which is autogenous to the reaction mixture. This is because hydrofluoric acid has a boiling point which is sufficiently low for it to be able, at the reaction temperatures, according to the pressure, to partially or completely pass into the gas phase. Consequently, in the phases (in the time sense) in which the operation is carried out at a temperature greater than the boiling point, it is necessary to maintain a higher pressure than atmospheric pressure.

Another solution consists in carrying out the reaction in the presence of a solvent. Use may in particular be made of aromatic solvents, especially aromatic solvents which are depleted in electrons, in order to avoid reactions between the carbamoyl fluoride and the aromatic nucleus of the solvent. Haloaromatic compounds, such as the various mono-, di- or trichlorobenzenes, are well suited to this type of dilution.

However, the advantage of the use of these solvents is insufficient for them to be used systematically; this use is only of significant advantage from the viewpoint of a subsequent stage.

Polar aprotic solvents can also give good results. However, they are not preferred.

If that which has been expanded upon above is summarized, the optimum batchwise process comprises 3 phases (in the time sense), namely:
- an exchange phase at relatively low temperature (see above),
- a temperature rise phase, in which phase the addition of water is generally situated (see above),
- a finishing phase at relatively high temperature (see above).

Thus, according to a particularly advantageous implementation of the present invention, the process consists:
a) in adding the isocyanate or the halide, advantageously carbamoyl fluoride, to liquid hydrofluoric acid, advantageously, if the operation is carried out at atmospheric pressure, at a temperature at most equal to approximately 10° C. (approximately is placed here in order to indicate that this value is rounded off mathematically);
b) optionally, once the addition has been carried out, the reaction mixture is gradually brought to a temperature of between ambient temperature (approximately 20° C.) and approximately 40° C.;
c) the reaction mixture is maintained in the temperature range of the preceding stage (a or b) for a period of time sufficient for there only to be at most a single, advantageously at most 0.1, chlorine atom to be exchanged with fluorine;
d) the reaction mixture is subsequently brought to a temperature of greater than 40° C. while the water is gradually added. This water results in an increase in the temperature which, in conjunction with the heating operation, brings the reaction mixture to a temperature within the range [70, 150], more often the range [70, 100]° C. (2 significant figures). The reaction mixture is maintained at this temperature until the time when the reaction is finished, which is determined by the absence of evolution of carbon dioxide gas.

The process can also be implemented continuously or in a "plug flow" reactor.

If the operation is carried out continuously, it is desirable to use at least 2 reactors:
- in the first, the first phase, namely the mixing and exchange, is implemented; substrate and reagents are introduced therein, advantageously continuously, the residence time in the reactor is advantageously adjusted so that there is only at most 0.2, preferably at most 0.1, halogen atom remaining to be exchanged, before changing reactor, the temperature range to be observed is that as defined for the introduction and the exchange;
- in the second reactor, when there are only two thereof, the water is introduced and the reaction is brought to completion at a temperature at least equal to 50° C., advantageously to 70° C., preferably to 90° C., indeed even to 100° C., and generally at most equal to 170° C., advantageously to 150° C., preferably to 130° C.

It may be advantageous to provide a third reactor, into which the water is introduced and which will be situated between the first and the second; in this third reactor, the temperature of which will be situated between the temperature of the first reactor and of the "second", advantageously between 40 and 130° C., will take place the beginning of the hydrolysis and thus the introduction of the water; which hydrolysis will be brought to completion in the said "second" reactor. This addition of an intermediate reactor between the first and second makes it possible in particular to operate in the high range of the finishing temperature (advantageously from 90 to 150° C., preferably from 100 (2 significant figures) to 130° C.).

According to another embodiment of the invention, the process can be carried out in a reactor of plug flow type, which theoretically behaves like an infinity of individual reactor with a volume δV moving in a reactor with a generally constant cross section, like a piston in a cylinder, and being subjected during its movement to the conditions, additions and conversions to which is subjected the reaction medium of a reactor operating under batchwise conditions.

The shape of these plug flow reactors is generally cylindrical, which implies a circular cross section, but it is possible to imagine other cross sections (for example, elliptical or polygonal). Thus, for example at the inlet, the reaction medium is composed of hydrofluoric acid, of the optional solvent and of the substrate; when it has been subjected to a movement corresponding to the time necessary for a sufficient change (see above), it then enters, during its movement, the temperature rise phase, during which the water is added; the remainder of the movement of the medium then corresponds to the finishing stage. In order to take into account the existence of a gas phase at the commonest working pressures, it is preferable to anticipate that the upper part of the reactor will be gaseous and thus that the reactor will not be completely filled with liquid, which implies that only the liquid part of the reactor may be categorized more or less as a plug flow reactor.

As was mentioned at the beginning of the present description, the present invention is essentially targeted, as substrate, at isocyanates and isocyanate derivatives (carbamoyl halide) exhibiting both an aryl nucleus carrying the nitrogen of the isocyanate functional group or of the carbamoyl halide functional group and a perhalogenated, generally perchlorinated, carbon atom with an sp³ nature, for the purpose of converting it to perfluorinated carbon.

This carbon must be situated in a position close to a doublet which is supposed to stabilize carbocations (without the mechanism of the reaction necessarily involving the formation of a carbocation; the Applicant Company has a poor understanding of the mechanisms of this exchange). This doublet can equally well be an unsaturation and in particular the carbons targeted here are carbons with an sp³ nature which are in the benzyl position with respect to an aromatic nucleus and especially sp³ carbons bonded directly to the aryl nucleus of the definition.

The doublet can also be provided by a chalcogen atom or be situated in the alpha position with respect to a double bond capable of activating the chlorine/fluorine exchange on the said sp³ atom. This type of conjugation is explained in European Patent Application EP 729 930 on behalf of the Applicant Company. For their part, the derivatives which can be activated by the presence of an unsaturation, or more generally of a double bond, are disclosed in Application WO 97/43231.

According to the present invention, it is highly desirable for the aromatic nucleus carrying the nitrogen of the isocyanate functional group or of the carbamoyl halide functional group not to carry nitro functional groups. This is because the nitro functional groups interfere with the reaction and result in many by-products.

More generally, it is preferable for the substrate molecule not to comprise any nitro functional group. The aliphatic carbon to be substituted is generally a trihalomethyl, which will result in a trifluoromethyl.

The total number of carbons in the substrate molecule is advantageously at most equal to 25, preferably to 15.

It is preferable for the aromatic nucleus to be depleted in electrons, that is to say for the sum of the Hammett constants $\sigma_p$ of the substituents of the said nucleus, not taking into account the nitrogen functional group which is part of the isocyanate functional group or of the functional groups deriving therefrom, to be greater than 0, advantageously greater than or equal to 0.15, more preferably to 0.25.

Reference may be made, for the Hammett constants, to the reference work on organic chemistry, namely Advanced Organic Chemistry, 3rd Edition, by Jerry March, published by John Wiley and Sons in 1985.

The sp³ carbon carrying the halogens to be exchanged comprises at least 2 halogens.

The substrates which can be used, in their carbamoyl fluoride form, according to the present invention can preferably be of formula:

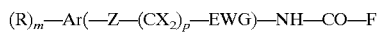

In this formula, the corresponding aniline part has the formula:

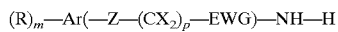

where:

Ar is an aromatic nucleus, preferably a homocyclic aromatic nucleus;

the X units, which are alike or different, represent a fluorine or a radical of formula $C_nF_{2n+1}$ with n an integer at most equal to 5, preferably to 2;

p represents an integer at most equal to 2;

EWG represents a hydrocarbonaceous group, an electron-withdrawing group, the possible functional groups of which are inert under the reaction conditions, advantageously fluorine, or a perfluorinated residue of formula $C_nF_{2n+1}$ with an integer at most equal to 8, advantageously to 5;

the total carbon number of $-(CX_2)_p-$EWG is advantageously between 1 and 15, preferably between 1 and 10;

m is 0 or an integer chosen within the closed interval (that is to say comprising the limits) 1 to 4;

R is a substituent which is inert under the operating conditions and which is advantageously chosen from halogens, advantageously light halogens (that is to say chlorine and fluorine), and hydrocarbonaceous radicals, preferably alkyl, aryl, alkylchalcogenyl (such as alkyloxyl) or arylchalcogenyl (such as aryloxyl) radicals;

Z represents a single bond or a chalcogen atom, advantageously a light chalcogen atom (sulphur and oxygen).

It is preferable for Ar advantageously to be monocyclic, preferably with 6 ring members.

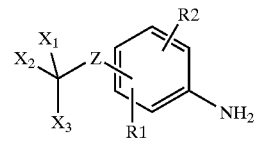

In particular, the aniline corresponding to the substrate can correspond to the formula:

where:

Z represents a single bond or a chalcogen atom, where $X_1$, $X_2$ and $X_3$ represent halogens which are alike or different, with the condition that at least 2 halogens are other than fluorine;

$R_1$ and $R_2$ are substituents from halogens, alkyls, aryls or nitrites.

The $X_3$ radical can be an electron-withdrawing group which does not interfere with the reaction and in particular can be a perfluorinated group, generally denoted $R_f$ in this area of technology.

The substrate compound can in particular have the formula (optional substituents which are inert under the reaction conditions do not appear) of the compounds of the following equations:

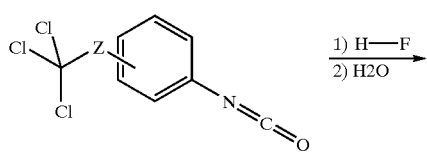

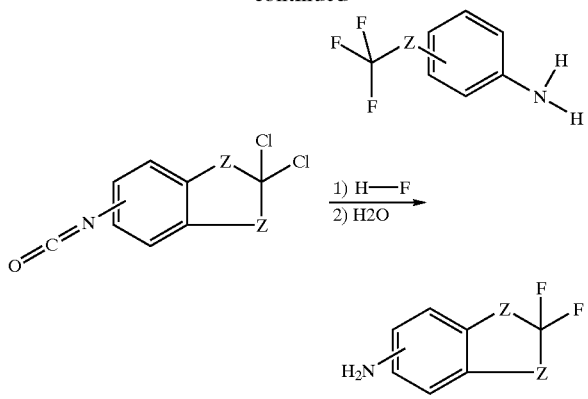

In the 2nd equation, the Z units, which are alike or different, represent a chalcogen, advantageously light chalcogens (sulphur and especially oxygen).

The following nonlimiting examples illustrate the invention.

EXAMPLE 1

HF (9 mol) is introduced into a reactor at a temperature of −5° C. The trichloromethylphenyl isocyanate (1 mol) which it is desired to convert is then introduced and the fluorination lasts 1 hour 30 at a temperature of 20° C.

A finishing operation is carried out at a temperature of 45° C. for 2 hours. It is observed that there then remains less than 0.1 chlorine atom to be exchanged.

The water (1.05 mol) is added; the temperature rises to 80° C. over 1 hour.

The mixture is then heated in order to bring the temperature to and to maintain it at 90° C. for 2 hours.

The isolated yield after neutralization and distillation is 93%.

EXAMPLE 2

(Comparative) Effect of Insufficient HF

HF (3.45 mol) is introduced into a reactor at a temperature of −0° C. The HF is heated to 10° C.; the trichloromethylphenyl isocyanate (0.54 mol, 127.7 g) which it is desired to convert is then introduced and the fluorination lasts 2 hours at a temperature of 10° C.

Thus, during the introduction, the HF/carbamoyl fluoride ratio is equal to 5.4; after complete exchange, it is only 2.4.

The reaction medium is heated to 100° C. and 0.81 mol of water is introduced during the rise in temperature between 70 and 80° C. The hydrolysis reaction is continued for 1 hour and 30 min at 100° C. The reaction medium is then cooled to 10° C., run onto a mixture of water and ice, and neutralized with an aqueous potassium hydroxide solution and the pTFMA is extracted with dichloromethane. The dichloromethane solution comprises 52 g of pTFMA, i.e. a yield of 60%.

EXAMPLE 3

Role of the Time at which the Water is Introduced

Water (0.614 mol) and HF (5.05 mol) are introduced into a reactor at a temperature of 0° C. The mixture is heated to 10° C. The trichloromethylphenyl isocyanate (0.414 mol, 97.9 g) which it is desired to convert is then introduced over approximately 15 minutes while maintaining the temperature at 10° C. The fluorination is continued for 1 hour at a temperature of 10° C.

The reaction medium is heated to 100° C. The hydrolysis reaction is continued for 1 hour at 100° C. The reaction medium is then cooled to 10° C., run onto a mixture of water and ice, and neutralized with an aqueous potassium hydroxide solution and the pTFMA is extracted with dichloromethane. The dichloromethane solution is analysed by HPLC; it comprises 49 g of pTFMA, i.e. a yield of 73.5%.

EXAMPLE 4

HF (6.62 mol) is introduced into a reactor at a temperature of −0° C. The HF is heated to 10° C. The trichloromethylphenyl isocyanate (0.544 mol, 128.6 g) which it is desired to convert is then introduced over approximately 15 min and the fluorination lasts 1 hour at a temperature of 10° C.

The reaction medium is gradually brought to 100° C. When the temperature at reached 70° C., it is confirmed that the exchange is complete (that is to say that the residual Cl is less than 2% in terms of equivalents). 0.88 mol of water is introduced during the rise in temperature between 70 and 90° C. The hydrolysis reaction is continued for 1 hour at 100° C. The reaction medium is then cooled to 10° C., run onto a mixture of water and ice, and neutralized with an aqueous potassium hydroxide solution and the pTFMA is extracted with dichloromethane. The dichloromethane solution is concentrated by evaporating the dichloromethane. 92.3 g of an oil are obtained, which oil comprises 93.7% of pTFMA, i.e. a yield of greater than 98.6%.

What is claimed is:

1. A process for the preparation of a compound comprising both a perfluorinated carbon and an aniline functional group from an aryl carbamoyl fluoride compound comprising chlorine atoms in place of the fluorine atoms on the perfluorinated carbon to obtain a partial exchange leaving at most one chlorine atom to be exchanged by molecule, said process comprising the steps of:

a) reacting said aryl carbamoyl fluoride compound at a temperature of between −10° C. and 40° C. in a reaction mixture comprising hydrofluoric acid and water in a liquid phase with a ratio of hydrofluoric acid to the aryl carbamoyl fluoride being maintained during the reaction at a value at least equal to 4 and at most equal to 11 to obtain the compound comprising both a perfluorinated carbon and an aniline functional group, b) bringing said temperature at a value of between 30° C. and 50° C. and, then, adding water, c) increasing said temperature to a value of between 70° C. and 100° C., and d) recovering the compound comprising both a perfluorinated carbon and an aniline functional group obtained in step a).

2. A process according to claim 1, wherein said ratio value is at least equal to 5.

3. A process according to claim 1, wherein the compound comprising both a perfluorinated carbon and an aniline functional group, has the formula:

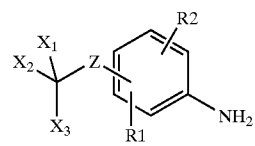

wherein $X_1$, $X_2$ and $X_3$ represent fluorine atoms, $R_1$ and $R_2$ are halogens, alkyls, aryls or nitriles, and Z represents a single bond, a sulphur atom, or an oxygen atom.

4. A process according to claim 1, wherein the partial exchange leaves at most 0.2 chlorine atom to be exchanged by molecule.

5. A process according to claim 1, wherein the partial exchange leaves at most 0.02 chlorine atom to be exchanged by molecule.

* * * * *